(12) United States Patent
Marcuccio et al.

(10) Patent No.: US 6,515,160 B2
(45) Date of Patent: Feb. 4, 2003

(54) BORONIC COMPOUNDS

(75) Inventors: Sebastian Mario Marcuccio, Endeavour Hills (AU); Mary Rodopoulos, Burwood East (AU); Helmut Weigold, Mount Waverley (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 09/982,858

(22) Filed: Oct. 22, 2001

(65) Prior Publication Data

US 2002/0052522 A1 May 2, 2002

Related U.S. Application Data

(62) Division of application No. 09/581,216, filed as application No. PCT/AU98/01072 on Dec. 23, 1998, now Pat. No. 6,346,639.

(30) Foreign Application Priority Data

Dec. 23, 1997 (AU) .............................................. PP1100
Feb. 26, 1998 (AU) .............................................. PP2026

(51) Int. Cl.$^7$ ................................................. C07F 5/04
(52) U.S. Cl. ...................... 558/290; 558/286; 558/292
(58) Field of Search ................................ 558/286, 288, 558/290, 292; 555/287

(56) References Cited

U.S. PATENT DOCUMENTS 2,965,582 A * 12/1960 Visnapuu
3,009,941 A * 11/1961 Brotherton et al.
3,062,823 A * 11/1962 McCloskey et al.
3,089,895 A * 5/1963 Newsom et al.

OTHER PUBLICATIONS

Inorg Chem by Lawlor et al vol. 37 pp. 5282–5288, Sep. 1998.*

J Org Chem by Nakamura et al vol. 63 pp. 7529–7530, Sep. 1998.*

J Org Chem by Malan et al vol. 63 pp. 8019–8020, Oct. 1998.*

Chemical Abstracts Accession No. 121:270436, Loderer et al., "Contribution to the chemistry of boron . . . ", Chem. Ber. (1994).

Chemical Abstracts Accession No. 105:42883, Noeth et al., "Chemistry of boron. 174 . . . ", Chem. Ber. (1986).

Chemical Abstracts Accession No. 110:146297, Yamada et al., "Borodiresorcylic acid–containing electrolytes for electrolytic capacitors", Jpn. Kokai Tokkyo Koho.

Chemical Abstracts Accession No. 108:75621, Brock et al., "Pyrazole derivatives of diborane (4)", J. Am. Chem. Soc. (1988).

Chemical Abstracts Accession No. 77:34615, Melcher et al., "Preparation and spectral characterization of unsymmetrically substituted borazines", Inorg. Chem. (1972).

Chemical Abstracts Accession No. 76:67582, Hessett et al., "Preparation, physical and spectroscopic . . . Me2N4BBN4Me2", J. Chem. Soc., Dalton Trans. (1972).

Chemical Abstract Accession No. 98:10688, Andrae et al., "1, 3, 2–Benoxathiaboroles", Z. Anorg. Allg. Chem. (1982).

Chemical Abstract Accession No. 124:117579, Moezzi et al., "Synthesis and structural characterization of [PhE(B-NMe2)2]2 (E×P or As) . . . ", Z. Anorg. Allg. Chem. (1995).

Chemical Abstracts Accession No. 116:186615, Bezuglaya et al., "Effect of substitution . . . with diboron tetraacetate", Zh. Obshch. Khim. (1991).

Chemical Abstracts Accession No. 72:21218, Brubaker et al., "Boron heterocycles. VI . . . ", Inorg. Chem. (1969).

Chemical Abstracts Accession No. 95:111718, Leifertova et al., "The antifungal properties of higher plants . . .", Folia Pharm. (Prague) (1979).

Chemical Abstracts Accession No. 68:56112, Welch et al., "Boron heterocycles. V. Preparation . . . ", Inorg. Chem. (1968).

Chemical Abstract Accession No. 93:168193, Koehn et al., "Chemistry of the I–aza–2–boro–3–oxacyclopentane system", Z. Naturforsch., B: Anorg. Chem., Org. Chem. (1980).

Chemical Abstract Accession No. 126:165744, Marder et al., "Reaction between rhodium (III) bisboryls and diborane (4) compounds . . . ", Chem. Commun. (Cambridge) (1997).

Chemical Abstract Accession No. 129–325339, Lawlor et al., "Bis–Catecholate, Bis–Dithiocatecholate and Tetraalkoxy Diborane (4) Compounds . . . ", Inorg. Chem. (1998).

Chemical Abstract Accession No. 129–302822, Nakamura et al., "A Concise Sythesis of Enantiomerically Pure L–(4–Boronophenyl) alanine from L–Tyrosine", J. Org. Chem. (1998).

Chemical Abstracts Accession No. 128:200027, Clegg et al., "Oxidative addition of boron–boron, boron–chlorine and boron–bromine bonds to platinum (O)", J. Organomet. Chem. (1998).

Chemical Communications by T.B. Marder et al., pp. 53–54, Jan. 1997.

Beilstein Registry No.: 2801373, prep abstract, J. Chem. Soc. by Beyer et al., pp. 2115–2118, 1964.

CA:115:183400 abs. Chem. Ber. by Heinrich et al., 124(9), pp. 1963–72, 1991.

CA:128:200027 abs. of J. Organomet. Chem. by Clegg et al., 550(1–2) pp. 182–192, 1998.

Beilstein Registry No.: 880147 abs of prep, J. Chem. Soc. by Brown et al., pp. 4648–4652, 1962.

(List continued on next page.)

Primary Examiner—Jean F. Vollano
(74) Attorney, Agent, or Firm—Bacon & Thomas PLLC

(57) ABSTRACT

A process for the preparation of a diboronic acid ester comprising contacting diboronic acid with a suitable monoalcohol, diol or polyol, for a time and under conditions such that the diboronic acid reacts with the monoalcohol, diol or polyol to form the diboronic acid ester.

6 Claims, No Drawings

OTHER PUBLICATIONS

Chemical Communications by T.B. Marder et al pp. 53–54, Jan. 1997.*

Beilstein Registry No.:2801373 prep abstract J Chem Soc by Beyer et al pp. 2115–2118, 1964.*

CA:115:183400 abs Chem Ber by Heinrich et al 124(9) pp. 1963–72, 1991.*

CA:128:200027 abs of J Organomet Chem by Clegg et al 550(1–2) pp. 183–192, 1998.*

Beilstein Registry No. : 880147 abs of prep J Chem Soc by Brown et al pp. 4648–4652, 1962.*

* cited by examiner

BORONIC COMPOUNDS

This application is a divisional application of U.S. application Ser. No. 09/581,216, filed Dec. 6, 2000, now U.S. Pat No. 6,346,639 (of which the entire disclosure of the pending, prior application is hereby incorporated by reference), which is a 371 of PCT/AU98/01072, filed Dec. 23, 1998, and which was published in English.

The invention relates to boronic compounds, in particular to novel diboron derivatives and organic boronic acid derivatives prepared therefrom. The invention also relates to processes for the preparation of these derivatives. These diboron derivatives and organic boronic acid derivatives are useful intermediates in processes for covalently linking organic compounds.

Processes for forming covalent bonds between organic compounds, both inter- and intra-molecular, are of particular importance to the synthetic organic chemist. Many such reactions are known, each requiring its own special reaction conditions, solvents, catalysts, ring activating groups etc. Some known types of coupling reactions include the Grignard reaction, Heck reactions and Suzuki reactions (N. Migaura and A. Suzuki, Chem. Rev. 1995, 95, 2457–2483).

Substituted bi- and tri-aryl compounds are of great interest to the pharmaceutical and agrochemical industries. A great number of these compounds have been found to possess pharmaceutical activity, while others have been found to be useful herbicides. There is also interest from the polymer industry in polymers prepared by the linking together of organic compounds.

Conventional methods for covalently linking aromatic rings, such as by reaction of an appropriate Grignard reagent, involve harsh conditions and are not suitable for aromatic rings with active hydrogen containing substituents. Substituents with active hydrogen atoms also can become involved in unwanted side reactions leading to undesirable products. Such substituents need to be protected prior to reaction. Boronic acid derivatives required for the Suzuki reaction are traditionally synthesized through highly reactive organo metallic intermediates.

In view of the severity of the reaction conditions the range of substituents which could be present during the linking reaction was considerably limited, and the range of useful reaction media (solvents) was restricted to those which can be expensive, difficult to remove and/or toxic.

A difficulty associated with the known coupling reactions is the limited control of the functionality of the products, leading to complex mixtures which can be difficult to separate.

Some known diboron derivatives are relatively unstable compounds, which decompose readily in aqueous solution or on exposure to air. For this reason, and a perceived difficulty in making the compounds, their use in chemical reaction is relatively unexplored.

It has now been found that diboron derivatives can be quite stable and useful in the preparation of organic boronic acid derivatives, and that properties of the diboron derivatives can be adjusted to suit particular reaction conditions or to provide particular products by selection of appropriate substituents.

Accordingly in a first aspect of the present invention there is provided a diboron derivative of formula (I)

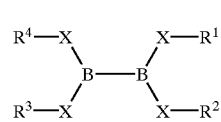

where

R$^1$, R$^1$, R$^3$ and R$^4$ are each independently selected from the group consisting of optionally substituted allyl, optionally substituted alkenyl, optionally substituted aryl, optionally substituted cycloalkyl, optionally substituted cycloalkenyl, and a group of the formula —(R$^5$Q)$_m$ R$^6$ where Q is selected from O, S, NR$^7$, optionally substituted arylene and optionally substituted cycloalkylene, m is an integer from 1 to 3, the or each R$^5$ is independently an optionally substituted C$_1$–C$_3$ alkylene, R$^6$ is C$_1$–C$_3$ alkyl or hydrogen and R$^7$ is hydrogen or C$_1$–C$_{12}$ alkyl; and each X is independently selected from O, S(O)$_n$ and NR$^7$, where n is an integer of 0 to 3 and R$^7$ is hydrogen or C$_1$–C$_{12}$ alkyl, or one or more of —NR$^1$R$^7$, —NR$^2$R$^7$, —NR$^3$R$^7$ and —NR$^4$R$^7$ represent an optionally substituted 5 or 6 membered heterocyclyl group, provided that when each X is O and R$^1$ to R$^4$ are identical, R$^1$ to R$^4$ are not unsubstituted straight chain akyl, phenyl or naphthyl, isopropyl, or phenyl substituted with alkyl; when each X is N(C$_1$–C$_6$ alkyl), R$^1$ to R$^4$ are not C$_{1-C6}$ alkyl and —NR$^1$R$^7$, —NR$^2$R$^7$, —NR$^3$R$^7$ and —NR$^4$R$^7$ are not unsubstituted piperidyl or unsubstituted pyrolidinyl; when each X is NH, R$^1$ to R$^4$ are not C$_1$–C$_6$ alkyl or unsubstituted phenyl; and when —XR$^1$ is —OCH$_3$, —XR$^2$ is —N(CH$_3$)$_2$ and —XR$^4$ is —N(CH$_3$)$_2$, —XR$^3$ is not OCH$_3$.

In a second aspect of the invention there is provided a diboron derivative of formula (II)

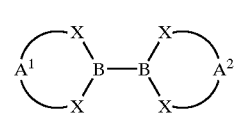

where X is independently selected from O, S(O)$_n$ and NR$^7$ where n is an integer from 0 to 2, R$^7$ is hydrogen or C$_1$–C$_{12}$ alkyl, and A$^1$ and A$^2$ are divalent groups which may be the same or different, provided that when each X is O, A$^1$ and A$^2$ are not unsubstituted C$_1$–C$_3$ alkylene, 1,1,2,2-tetramethylethylene, 2,2-dimethylpropylene, 1,2-dialkoxycarbonylethylene, 1,2 diphenylethylene, 1 phenylethylene, unsubstituted phenylene or phenylene mono- or di-substituted with C$_1$–C$_4$ alkyl; and when each X is S or NMe, both of A$^1$ and A$^2$ are not ethylene.

Preferably A$^1$ and A$^2$ are independently selected from optionally substituted alkylene, optionally substituted alkenylene, optionally substituted alkynylene, optionally substituted arylene, optionally substituted alkylarylene, optionally substituted cycloalkylene, optionally substituted cycloalkenylene, or a group of the formula —(R$^5$Q)$_m$R$^6$ where Q is selected from O, S, NR$^7$, optionally substituted arylene and optionally substituted cycloalkylene, m is an integer of 1 to 3, R$^5$ and R$^6$ are independently an optionally substituted C$_1$–C$_3$ alkylene, and R$^7$ is hydrogen or C$_1$–C$_{12}$ alkyl. The divalent groups, A$^1$ and A$^2$, may include a fused 5 or 6 membered aliphatic or aromatic ring.

In a third aspect of the present invention there is provided a diboron derivative of formula

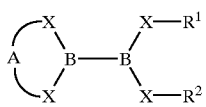

where

R$^1$ and R$^2$ are each independently selected from the group consisting of optionally substituted alkyl, optionally substituted alkenyl, optionally substituted alkynyl, optionally substituted aryl, optionally substituted cycloalkyl, optionally substituted cycloalkenyl, a group of the formula —(R$^5$Q)$_m$R$^6$ where Q is selected from O, S, NR$^7$, optionally substituted arylene and optionally substituted cycloalkylene, m is an integer of 1 to 3, the or each R$^5$ is independently an optionally substituted C$_1$–C$_3$ alkylene, R$^6$ is hydrogen or C$_1$–C$_3$ alky, and R$^7$ is hydrogen or C$_1$–C$_{12}$ alkyl;

each X is independently selected from O, S(O)$_n$ and NR$^7$, where n is an integer of 0 to 3 and R$^7$ is hydrogen or C$_1$–C$_{12}$ alky, or one or both of —NR$^1$R$^7$ and —NR$^2$R$^7$ represent an optionally substituted 5 or 6 membered heterocyclyl group; and A is a divalent group;

provided that when R$^1$ and R$^2$ are Me and each X is NMe then A is not unsubstituted ethylene.

Preferably A is independently selected from optionally substituted alkylene, optionally substituted alkenylene, optionally substituted arylene, optionally substituted cycloalkylene, optionally substituted cycloalkenylene, or a group of the formula —(R$^5$Q)$_m$R$^6$— where Q is selected from O, S, NR$^7$, optionally substituted arylene and optionally substituted cycloalkylene, m is an integer of 1 to 3, R$^5$ and R$^6$ are independently an optionally substituted C$_1$–C$_3$ alkylene, and R$^7$ is hydrogen or C$_1$–C$_{12}$ alkyl. The divalent group A, may include a fused aliphatic or aromatic ring or ring system.

The invention also provides a diboron derivative of formula (I)

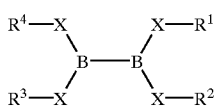

or a diboron derivative of formula (II)

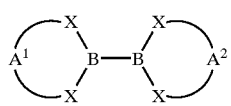

or a diboron derivative of formula (III)

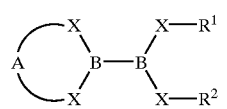

where

R$^1$, R$^2$, R$^3$ and R$^4$ are each independently selected from the group consisting of optionally substituted alkyl, optionally substituted alkenyl, optionally substituted aryl, optionally substituted cycloalkyl, optionally substituted cycloalkenyl, a group of the formula —(R$^5$Q)$_m$R$^6$ where Q is selected from O, S, NR$^7$, optionally substituted arylene and optionally substituted cycloalkylene, m is an integer of 1 to 3, the or and each R$^5$ is independently an optionally substituted C$_1$–C$_3$ alkylene, R$^6$ is C$_1$–C$_3$ alkyl or hydrogen, and R$^7$ is hydrogen or C$_1$–C$_{12}$ alkyl;

each X is independently selected from O, S(O)$_n$ and NR$^7$, where n is an integer from 0 to 3, R$^7$ is hydrogen or C$_1$–C$_{12}$ alkyl, or one or more of —NR$^1$R$^7$, —NR$^2$R$^7$, —NR$^3$R$^7$ and —NR$^4$R$^7$ represent an optionally substituted 5 or 6 membered heterocyclyl group, and A, A$^1$ and A$^2$ are divalent groups which may or may not be different, wherein said derivative has one or more chiral centres and there is an enantiomeric excess of one form.

Preferably the enantiomeric excess is greater than 80%, and more preferably greater than 90%.

In the above definitions, the term "alkyl", used either alone or in compound words such as "alkenyloxyalkyl", "alkylthio", "alkylarnino" and "dialkylamino" denotes straight chain or branched alkyl, preferably C$_{1-20}$ alkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methoxyhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3,-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 16 or 7-methyl-octyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2- 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl 1-2-pentylheptyl and the like.

The term "alkylene" denotes a divalent alkyl group as defined above.

The term "cycloalkyl" denotes cyclic alkyl groups, preferably C$_{3-20}$ cycloalkyl. Examples of cycloalkyl include mono- or polycyclic alkyl groups such as cyclopropyl, cyclobutyl, cyclopentyl, cyclohexyl, cycloheptyl, cyclooctyl, cyclononyl, cyclodecyl and the like.

The term "cycloalkylene" denotes a divalent cycloalkyl group as defined above.

The term "alkenyl" denotes groups formed from straight chain or branched alkenes including ethylenically mono-, di- or poly-unsaturated alkyl or groups as previously defined, preferably C$_{2-20}$ alkenyl. Examples of alkenyl include vinyl, allyl, 1-methylvinyl, butenyl, iso-butenyl, 3-methyl-2-butenyl, 1-pentenyl, 1-hexenyl, 3-hexenyl, 1-heptenyl, 3-heptenyl, 1-octenyl, 1-nonenyl, 2-nonenyl, 3-nonenyl, 1-decenyl, 3-decenyl, 1,3-butadienyl, 1-4,pentadienyl, 1,3-hexadienyl, 1,4-hexadienyl.

The term "alkenylene" denotes a divalent alkenyl group as defined above.

The term "cycloalkenyl" denotes cyclic alkene groups, preferably C$_{5-20}$ cycloalkenyl. Examples of cycloalkenyl include (cyclopentenyl, methyl cyclopentenyl, cyclohexenyl, cyclooctenyl, 1,3-cyclopentadienyl, 1,3-cyclohexadienyl, 1,4-cyclohexadienyl, 1,3-cycloheptadienyl, 1,3,5-cycloheptatrienyl and 1,3,5,7-cyclooctatetraenyl.

The term "cycloalkenylene" denotes a divalent cycloalkenyl group as defined above.

The term "aryl" is used herein in the broadest sense to refer to any aromatic ring or ring system, preferably having 3 to 20 carbon atoms. The ring or ring system may contain one or more heteroatoms selected from N, S, and O. The aromatic rings may be carbocyclic, heterocyclic or pseudo aromatic, and may be mono or polycyclic ring systems. Examples of suitable rings include but are not limited to benzene, biphenyl, terphenyl, quaterphenyl, naphthalene, tetrahydronaphthalene, 1-benzylnaphthalene, anthracene, dihydroanthracene, benzanthracene, dibenzanthracene, phenanthracene, perylene, pyridine, 4-phenylpyridine, 3-phenylpyridine, thiophene, benzothiophene, naphthothiophene, thianthrene, furan, pyrene, isobenzofuramn, chromene, xanthene, phenoxathiin, pyrrole, imidazole, pyrazole, pyrazine, pyrimidine, pyridazine, indole, indolizine, isoindole, purine, quinoline, isoquinoline, phthalazine, quinoxaline, quinazoline, pteridine, carbazole, carboline, phenanthridine, acridine, phenanthroline, phenazine, isothiazole, isooxazole, phenoxazine and the like, each of which may be optionally substituted. The term "pseudoaromatic" refers to a ring system which is not strictly aromatic, but which is stablized by means of delocalization of π electrons and behaves in a similar manner to aromatic rings. Examples of pseudoaromatic rings include but are not limited to furan, thiophene, pyrrole and the like.

The term "aliphatic ring or ring system" as used herein refers to a non-aromatic carbocyclic or heterocyclic ring or ring system, preferably having from 3 to 20 carbon atoms. The ring or ring system may have one or more double or triple bonds. Examples of suitable aliphatic rings include but are not limited to cyclobutane, cyclopentadiene, cyclohexanone, cyclohexene, spiro-[4,5-decane] and hydrogenated or partially hydrogenated aromatic rings as described above.

The term "arylene" as used herein denotes a divalent "aryl" moiety as defined above.

As used herein, an "olefinic" compound refers to any organic compound having at least one carbon to carbon double bond which is not part of an aromatic or pseudo aromatic system. The olefinic compounds may be selected from optionally substituted straight chain, branched or cyclic alkenes; and molecules, monomers and macromolecules such as polymers and dendrimers, which include at least one carbon to carbon double bond. Examples of suitable olefinic compounds include but are not limited to ethylene, propylene, but-1-ene, but-2-ene, pent-1-ene, pent-2-ene, cyclopentene, 1-methylpent-2-ene, hex-1-ene, hex-2-ene, hex-3-ene, cyclohexene, hept-1-ene, hept-2-ene, hept-3-ene, oct-1-ene, oct-2-ene, cyclooctene, non-1-ene, non-4-ene, dec-1-ene, dec-3-ene, buta-1,3-diene, penta-1,4-diene, cyclopenta-1,4-diene, hex-1,4,diene, cyclohexa-1,3-diene, cyclohexa-1,4-diene, cyclohepta-1,3-diene, cyclohepta-1,3,5-triene and cycloocta-1,3,5,7-tetraene, each of which may be optionally substituted. Preferably the straight chain branched or cyclic alkene contains between 2 and 20 carbon atoms.

In this specification "optionally substituted" means that a group may or may not be further substituted with one or more groups selected from alkyl, alkenyl, alkynyl, aryl, halo, haloalkyl, haloalkenyl, haloalkynyl, haloaryl, hydroxy, alkoxy, alkenyloxy, aryloxy, aryloxyalkyl, benzyloxy, haloalkoxy, haloalkenyloxy, haloaryloxy, isocyano, cyano, formyl, carboxyl, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, imino, alkylimino, alkenylimino, alkynylimino, arylimino, benzylimino, dibenzylamino, acyl, alkenylacyl, alkynylacyl, arylacyl, acylamino, diacylamino, acyloxy, alkylsulphonyloxy, arylsulphenyloxy, heterocyclyl, heterocycloxy, heterocyclamino, haloheterocyclyl, alkylsulphenyl, arylsulphenyl, carboalkoxy, carboaryloxy mercapto, alkylthio, benzylthio, acylthio, sulphonamido, sulfanyl, sulfo and phosphorus-containing groups.

The term "fused aliphatic or aromatic ring" as used herein in relation to divalent groups A, A and $A^2$ means that one or more of the bonds connecting the X moieties of the compounds of formulae I, II or III is part of an aliphatic or aromatic ring system.

As used herein the term "divalent group" refers to any group having two valencies available for bonding with another chemical moiety. Examples of suitable divalent groups include alkylene, alkenylene, cycloalkylene and the like.

The term "acyl" as used herein refers to carbamoyl, aliphatic acyl group and acyl group is referred to as heterocyclic acyl, preferably $C_{1-20}$ acyl. Examples of acyl include carbamoyl; straight chain or branched alkanoyl such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl and icosanoyl; alkoxycarbonyl such as methoxycarbonyl, ethoxycarbonyl, t-butoxycarbonyl, t-pentyloxycarbonyl and heptyloxycarbonyl; cycloalkylcarbonyl such as cyclopropylcarbonyl, cyclobutylcarbonyl, cyclopentylcarbonyl and cyclohexylcarbonyl; alkylsulfonyl such as methylsulfonyl and ethylsulfonyl; alkoxysulfonyl such as methoxysulfonyl and ethoxysulfonyl; aroyl such as benzoyl, toluoyl and naphthoyl; aralkanoyl such as phenylalkanoyl (e.g. phenylacetyl, phenylpropanoyl, phenylbutanoyl, phenylisobutylyl, phenylpentanoyl and phenylhexanoyl) and naphthylalkanoyl (e.g. naphthylacetyl, naphthylpropanoyl and naphthylbutanoyl]; aralkenoyl such as phenylalkenoyl (e.g. phenylpropenoyl, phenylbutenoyl, phenylmethacryloyl, phenylpentenoyl and phenylhexenoyl and naphthylalkenoyl (e.g. naphthylpropenoyl, naphthylbutenoyl and naphthylpentenoyl); aralkoxycarbonyl such as phenylalkoxycarbonyl (e.g. benzyloxycarbonyl); aryloxycarbonyl such as phenoxycarbonyl and napthyloxycarbonyl; aryloxyalkanoyl such as phenoxyacetyl and phenoxypropionyl; alkylcarbamoyl such as phenylcarbamoyl; arylthiocarbamoyl such as phenylthiocarbamoyl; arylglyoxyloyl such as phenylglyoxyloyl and naphthylglyoxyloyl; arylsulfonyl such as phenylsulfonyl and napthylsulfonyl; heterocycliccarbonyl; heterocyclicalkanoyl such as thienylacetyl, thienylpropanoyl, thienylbutanoyl, thienylpentanoyl, thienylhexanoyl, thiazolylacetyl, thiadiazolylacetyl and tetrazolylacetyl; heterocyclicalkenoyl such as heterocyclicpropenoyl, heterocyclicbutenoyl, heterocyclicpentenoyl and heterocyclichexenoyl; and heterocyclicglyoxyloyl such as thiazolylglyoxyloyl and thienylglyoxyloyl.

The diboron derivatives may be made following the method of Brotherton et al. [R. J. Brotherton, A. L. McCloskey, L. L. Peterson and H. Steinberg, *J. Amer. Chem.*

Soc. 82, 6242 (1960); R. J. Brotherton, A. L. McCloskey, J. L. Boone and H. M. Manasevit, *J. Amer. Chem. Soc.* 82, 6245 (1960)]. In this process $B(NMe_2)_3$, obtained by reaction of $BCl_3$ with $NHMe_2$, is converted to $BrB(NMe_2)_2$ by reaction with a stoichiometric amount of $BBr_3$. Reduction in refluxing toluene with sodium metal gives the diboron compound $[B(NMe_2)_2]_2$ which, after purification by distillation, can be reacted with the alcohol (for example, pinacol or neopentanediol) in the presence of a stoichiometric amount (four equivalents) of HCl to give the desired ester product.

With many alcohols this reaction is unsatisfactory, the reaction being slow and complete removal of the amine being difficult unless anhydrous mineral acid (four equivalents) are added to the reaction.

An aspect of the present invention is the discovery that esters of tetrahydroxydiboron can be readily synthesised in near quantitative yield by the reaction of diboronic acid (tetrahydroxydiboron) with alcohols (including diols and polyols) and this reaction does not require the presence of acids. Furthermore, it has been found that the reaction of tetrahydroxydiboron with certain diols can be carried out with advantage in the presence of simple monoalcohols such as methanol or ethanol without these monoalcohols being incorporated in the final reaction products. These reactions, in the presence of monoalcohols, show that tetrahydroxydiboron esters of these monoalcohols readily undergo transesterification with diols that can form ring structures on a boron atom. The transesterification represents a further procedure for the production of esters of tetrahydroxydiboron. These reactions can be performed in a variety of solvents or mixtures thereof.

Accordingly in a further aspect of the present invention there is provided a process for the preparation of a diboronic acid ester comprising contacting diboronic acid with a suitable monoalcohol, diol or polyol for a time and under conditions such that the diboronic acid reacts with the diol or polyol to produce the diboron derivative.

Unlike the literature procedure, the process according to this aspect of the present invention lends itself readily to the synthesis of tetrahydroxydiboron esters with acid sensitive alcohols. The synthesis of tetrahydroxydiboron esters with alcohols possessing basic functionalities are difficult using the known literature method since the products obtained are partially or fully protonated on their basic functionalities. The process according to this aspect of the present invention does not have this inherent problem.

In the prior art procedure the side product, the acid salt of the amine, must be removed to obtain pure product. A major advantage of the present process is that product obtained is sufficiently pure that it can generally be used without the need for further purification.

The diboron derivatives according to the present invention are useful in the preparation of organic boronic acid derivatives, and by selection of appropriate substituents and reactants, it is possible to use the diboron derivatives to form organic boronic acid derivatives which are useful in organic coupling reactions.

The organic boronic acid derivatives are generally prepared by reaction of a diboron derivative of this invention and an organic compound in the presence of a Group VIII metal catalyst. In order to participate in such a reaction the organic compound should possess a boron reactive site.

The boron reactive site may be a halogen or halogen-like substituent on the organic compound, a carbon to carbon double or triple bond, or leaving group located in an allylic position.

In the case of halogen or halogen-like substituents, and allylic leaving groups, the diboron derivative displaces the group in a substitution reaction to form an organic boronic acid derivative. In the case of reaction with double and triple carbon-to-carbon bonds in the presence of platinum and like catalysts, the diboron compound tends to undergo an addition reaction across the double or triple bond to form products in which the boron esters are located on adjacent carbon atoms.

The terms "halogen-like substituent" and "pseudo-halide" refer to any substituent which, if present on an organic compound, may react with a diboron derivative in the presence of a Group VIII metal catalyst and base to give an organic boronic acid derivative. Preferred halogen substituents include I and Br. Cl may also be used although Cl is generally less reactive to substitution by the diboron compound. The reactivity of chloro substituted organic compounds can be increased by selection of appropriate ligands on the Group VIII metal catalyst. Examples of halogen-like substituents include triflates and mesylates, diazonium salts, phosphates and those described in Palladium Reagents & Catalysts (Innovations in Organic Synthesis by J. Tsuji, John Wiley & Sons, 1995, ISBN 0-471-95483-7).

As used herein, the term "leaving group" refers to a chemical group which is capable of being displaced by a boronic acid residue. Suitable leaving groups are apparent to those skilled in the art and include halogen and halogen-like substituents.

The temperature at which the preparation of the diboronic acid esters is conducted will depend on a number of factors including the desired rate of reaction, solubility and reactivity of the reactants in the selected solvent, boiling point of the solvent, etc. The temperature of the reaction will generally be in the range of −100 to 200° C. In a preferred embodiment the process is performed at a temperature between 0 and 80°, more preferably between 15 and 40° C.

Chiral diboronic acid derivatives may be prepared from chiral starting materials or intermediates under conditions in which the chirality is preserved or they may also be prepared via the racemate in which case a separation step will be required. Separation of the enantiomers may be achieved conventionally using conventional chromatographic methods including chiral chromatography, enzymatic resolution, or using a resolving agent. The individual chiral forms are also part of the present invention.

Diboron derivatives containing a chiral centre, if there is an enantiomeric excess of one isomer, are particularly useful in the preparation of enantiomers of chiral compounds. In this regard it is possible to react a diboron compound having one or more chiral centers, and an enantiomeric excess of one enantiomer, with an organic compound having a boron reactive site to produce an organic boronic acid ester derivative in which the chirality is preserved. The chiral organic boronic acid derivative may then be reacted with another organic compound to produce a new chiral centre, the stereochemistry of which is induced by the stereochemistry of the chiral organic boronic acid derivative. Suitable organic compounds with which to react the chiral organic boronic acid derivative include aldehydes and unsymmetrical ketones, as reaction at the carbonyl produces a new chiral center. It is also possible to couple sterically hindered aromatic rings via an aromatic boronic acid derivative intermediate to produce chiral biaryl compounds in which the helical sense is maintained through restricted rotation about the bond linking the aromatic rings (also referred to as atropism).

In a particularly preferred embodiment of the invention a diboron derivative is prepared by reacting a suitable diboron reactant with a chiral diol, examples include pinanediol, diisopropyl tartrate, and sugars, such as mannose or galactose and like sugars containing cis-hydroxy groups or other hydroxy groups suitably orientated to couple with boron. The chiral diboron derivatives may then be reacted with suitable organic compounds having boron reactive sites to produce chiral organic boronic acid derivatives. These may be reacted in a stereospecific manner with an organic compound, with the formation of a new chiral center.

It is also possible to activate the boron to boron bond by selecting an $R^1$ to $R^4$, A, $A^1$, or $A^2$ substituent which is capable of further coordinating with one of the boron atoms. Such groups would include an electron rich substituent or atom which is capable of feeding electron density onto the boron atom. Examples of electron rich atoms include oxygen, nitrogen and sulphur.

A difficulty with using the known pinacol ester of diboronic acid to produce organic boronic acids is that it is difficult to cleave the pinacol ester to give the corresponding organic boronic acid. Other esters of this invention have been found to hydrolyse more readily than the pinacol ester. Esters containing an aromatic ring on the carbon α to the X moiety are surprisingly easy to cleave to the corresponding boronic acid. Benzyl ester derivatives are particularly useful for this purpose.

It is also possible to select substituents to improve the solubility of the diboron derivative in a particular solvent in which a subsequent reaction is to be carried out. Water solubility of the diboron compound can be increased by introducing polar groups, such as hydroxy groups, into the $R^1$ to $R^4$, A, $A^1$ and $A^2$ substituents. Similarly it is possible to select substituents which increase the solubility of the diboron compound in the desired organic solvent.

Many of the boronic acid ester derivatives prepared from the novel diboronic acid derivatives according to the present invention are also novel and represent a further aspect of the present invention.

These organic boronic acid derivatives may be reacted with organic compounds having one or more boron reactive sites to produce coupled products, as described above. These coupling reactions are generally conducted in the presence of a group VIII metal catalyst and a suitable base.

The process and compounds according to the invention are also useful for the preparation of reactive intermediates which are capable of taking part in further reactions or rearrangements. These reactive intermediates may be the organic boronic acid derivative or the coupled products. For example, organic boronic acid derivatives may take part in one or more of the palladium catalysed reactions of organoboron compounds described by Miyaura and Suzuki in Chem. Rev. 1995, 95 2457–2483. Examples of other types of reactions in which the diboron derivatives of the present invention are useful are described in copending applications PCT/AU98/00245 and PCT/AU98/00476.

The invention will now be described with reference to the following examples which illustrate some preferred embodiments of the invention. It is to be understood that the particularity of the following description is not to supersede the generality of the preceding description of the invention.

EXAMPLES

General Procedures
General Procedure A

Two equivalents of diol is added to a solution of tetrakis (dimethylamino)diboron in dry diethyl ether under nitrogen. The reaction mixture is stirred magnetically and cooled in an ice-bath before adding a dry etheral solution of hydrogen chloride (4 equivalents) over 1 h. After stirring overnight at room temperature the reaction mixture is filtered and the solid collected is extracted with hot benzene (2×) to remove the dimethylamine hydrochloride salt. The ether filtrate and the benzene extracts are taken to dryness under vacuum. The resultant products are then combined, recrystallised from benzene/petroleum spirit (60–80° C.) and dried under high vacuum.

General Procedure B

Two equivalents of diol is added to diboronic acid in benzene and the reaction mixture heated under reflux for 24 hours using a Dean-Stark apparatus. The benzene solution is separated from the water formed, dried and taken to dryness under vacuum to give the diboronic ester. The addition of monoalcohols such as ethanol or methanol can be used to enhance this procedure.

General Procedure C

Two equivalents of diol is added to diboronic acid in tetrahydrofuran. A dehydrating agent such as anhydrous sodium sulphate is added and the reaction mixture stirred at room temperature overnight. The solution is then filtered and the filtrate taken to dryness under vacuum to yield the diboronic ester. The addition of monoalcohols such as methanol and ethanol can be used to enhance the procedure. The presence of a dehydrating agent is not always necessary for satisfactory yields.

Example 10

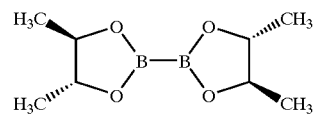

This diboronic ester is prepared following general procedure A using (2R,3R)-(−)-2,3-butanediol. $^1$H-nmr (CDCl$_3$, 200 MHz): δ1.22 (6H, multiplet; CHC$\underline{H}_3$) and 4.00 (2H, multiplet; C$\underline{H}$CH$_3$).

Example 2

1,1,2,2-Tetrakis(2-methoxyethyloxy)diborane

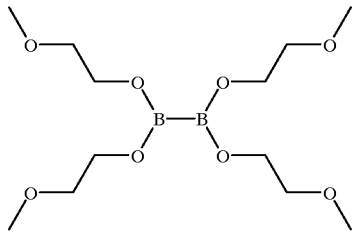

This diboronic ester is prepared following general procedure A using 2-methoxy-ethanol. $^1$H-nmr (CDCl$_3$, 200 MHz): δ3.36 (3H, singlet; C$\underline{H}_3$), 3.42–3.51 (2H, multiplet; BOC$\underline{H}_2$) and 3.62–3.71 (2H, multiplet; C$\underline{H}_2$O).

Example 3

Bis((1S,2S,3R,5S)-(+)-pinanediolato)diboron(B-B)

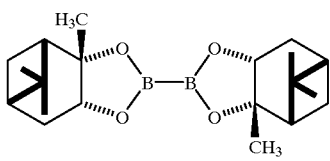

This diboronic ester is prepared following general procedure A using (1S,2S,3R,5S)-(+)-pinanediol. Yield 98% $^1$H-nmr (CDCl$_3$, 200 MHz): δ0.77 (singlet, 3H; C$_3$C$\underline{H}_3$), 1.01–1.13 (doublet, 2H; C$_3$C$\underline{H}$), 1.20 (3H, singlet; C$_3$C$\underline{H}_3$), 1.87–1.91 (2H, multiplet; C$_2$C$\underline{H}_2$), 1.92–2.31 (3H, multiplet; C$\underline{H}_2$CO and C$\underline{H}$CO) and 4.15–4.26 (1H, multiplet; C$_2$(C$\underline{H}$O).

Example 4

(4R,4'R)-Diphenyl-2,2'-bi-1,3,2-dioxaborolane

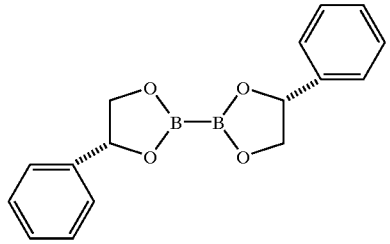

This diboronic ester is prepared following general procedure A using (R)-(−)-1-phenyl-1,2-ethanediol. Yield, 88% $^1$H-nmr (CDCl$_3$, 200 MHz): δ3.90–4.01 (1H, triplet; C$\underline{H}_2$C), 4.42–4.57 (1H, triplet; C$\underline{H}_2$C) and 7.10–7.31 (5H, multiplet; Ar$\underline{H}$). $^{13}$C-nmr (CDCl$_3$, 200 MHz): δ72.73 (1C; $\underline{C}$H$_2$), 78.78 (1C; $\underline{C}$Ph) 125.71 (2C; m-$\underline{C}$), 128.17 (1C; p-$\underline{C}$), 128.70 (2C; o-$\underline{C}$) and 140.65 (1C; $\underline{C}$-O).

Example 5

4,4'-Bi-[(4-methoxyphenoxy)methyl]-2,2-'bi-1,3,2-dioxaborolane

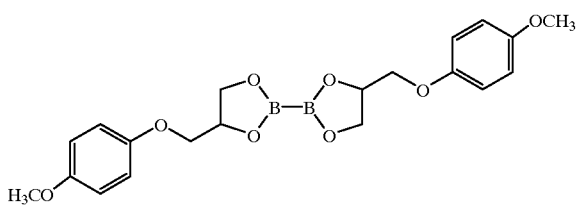

This diboronic ester is prepared following general procedure A using 3-(4-methoxyphenoxy)-1,2-propanediol. Yield, 70% $^{13}$C-nmr (D$_6$-DMSO, 200 MHz): δ55.27, 66.50, 70.00, 70.74, 74.80, 114.51, 115.45, 152.30 and 153.60.

Example 6

2,2'-Bi-(3aR,7aS)hexahydro-1,3,2-benzodioxaborole

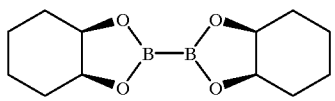

This diboronic ester is prepared following general procedure A using cis-1,2-cyclohexanediol. Yield, 65%. $^1$H-mnr (CDCl$_3$, 200 MHz): δ1.20–2.00 (multiplet, 8H; C$\underline{H}_2$ and 4.30 (multiplet, 2H; C$\underline{H}$).

Example 7

Tetraisopropyl (4R,4'R,5R,5'R)-2,2'-bi-1,3,2-dioxaborolane-4,4'5,5'-tetracarboxylate

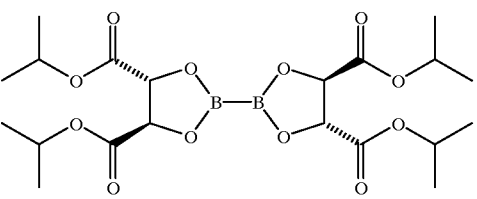

This diboronic ester is prepared following general procedure A using diisopropyl L-tartrate. Yield, quantitative. $^1$H-nmr (CDCl$_3$, 200 MHz): δ1.10–1.30 (multiplet, 28H; C$\underline{H}$CH$_3$ and C$\underline{H}_3$) and 4.30 (singlet, 4H; OC$\underline{H}$).

Example 8

(3aR,3'aR,6aS,6'aS)-Di-(tetrahydro-3aH-cyclopenta[d])-2,2'-bi-1,3,2-dioxaborolane

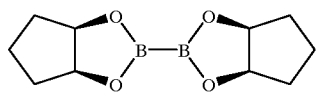

This diboronic ester is prepared following general procedure A using cis-1,2-cyclopentanediol. Yield, 78% $^1$H-nmr (CDCl$_3$, 200 MHz): δ1.40–1.61 (multiplet, 4H; OCHCH$_2$), 1.75–2.00 (multiplet, 2H; CH$_2$CH$_2$C$\underline{H}_2$) and 4.80 (multiplet, 2H; OC$\underline{H}$).

Example 9

3R,6S,3'R,6'S)-Di-(tetrahydrofuro[3,4d])-2,2'-bi-1,3,2-dioxaborolane

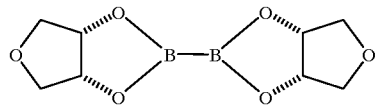

This diboronic ester is prepared following general procedure A using 1,4-anhydroerythritol. Yield, 78% $^1$H-nmr (CDCl$_3$, 200 MHz): δ3.40–3.50 (multiplet, 2H; OCH$\underline{H}$), 4.00–4.14 (multiplet, 2H; CH$\underline{H}$) and 4.90 (multiplet, 2H; OC$\underline{H}$).

Example 1

4,4'-Bis(methoxymethyl)-2,2'-bi-1,3,2-dioxaborolane

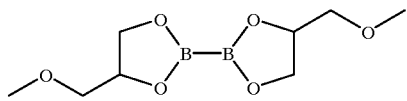

This diboronic ester is prepared following general procedure A using 3-methoxy-1,2-propanediol. Yield, 96% $^1$H-nmr (CDCl$_3$, 200 MHz): δ3.23 (singlet, 6H; OC$\underline{H}_3$), 3.30–3.40 (multiplet, 4H; CH$_3$OC$\underline{H}$H), 3.80–3.95 (multiplet, 2H; (multiplet, 2H; CH$_3$OCH$\underline{H}$), 4.10–4.20 (triplet, 2H; C$\underline{H}_2$OB) and 4.40–4.50 (multiplet, 2H; OC$\underline{H}$).

Example 11

2,2'-Bi-1,3,2-dioxaborepane

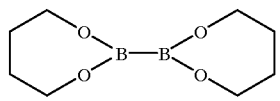

This diboronic ester is prepared following general procedure A using 1,4-butanediol. $^1$H-nmr (D$_6$-DMSO, 200 MHZ): δ1.36–1.42 (multiplet, 4H; CH$_2$C$\underline{H}_2$CH$_2$) and 3.36 (multiplet, 4H; CH$_2$O).

Example 12

5,5'-Dihydroxymethyl-5,5'-Dimethyl-2,2'-bi-1,3,2-dioxaborinane

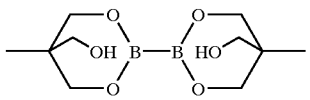

This diboronic ester is prepared following general procedure C using 1,1,1-tris(hydroxymethyl)ethane. Yield, 90% $^1$H-nmr (d$_6$dmso; 200 MHz): δ0.79 (singlet, 6H; 2×C$\underline{H}_3$), 3.21–3.75 (multiplet, 12H; 6×C$\underline{H}_2$O) and 4.76 (triplet, 2H; 2×O$\underline{H}$). F.W.: calc. for C$_{10}$H$_{20}$B$_2$O$_6$=257.89, found m/z 259 (M+1).

Example 13

Bis(1R,2R,3S,5R-(−)-pinanediolato)diboron(B—B)

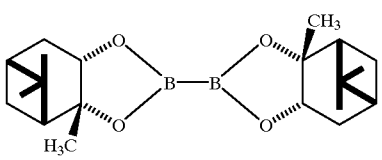

This diboronic ester is prepared following general procedure A using 1R,2R,3S,5R-(−)-pinanediol. Yield, 77%. $^1$H-nmr (CDCl$_3$, 200 MHz;): δ0.84 (singlet, 6H; 2×C$_3$C$\underline{H}_3$), 1.08–1.14 (doublet, 2H; 2×C$_3$C$\underline{H}$), 1.28 (singlet, 6H; 2×C$_3$CH$_3$), 1.39 (singlet, 6H; 2×C$\underline{H}_3$CO), 1.87–1.97 (multiplet, 4H; 2×C$_2$C$\underline{H}_2$), 2.04–2.37 (multiplet, 6H; 2×C$\underline{H}_2$CO and 2×C$\underline{H}$CO) and 4.24–4.29 (multiplet, 2H; 2×C$_2$C $\underline{H}$O). F.W.: calc. for C$_{20}$H$_{32}$B$_2$O$_4$=358.09, found m/z 359 (M+1).

Example 14

2,2'-Bi-4H-1,3,2-benzodioxaborinine

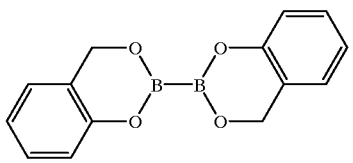

This diboronic ester is prepared following general procedure C using 2-hydroxybenzyl alcohol. Yield, 77%. $^1$H-nmr (CDCl$_3$, 200 MHz): δ5.12 (singlet, 4H; 2×ArC$\underline{H}_2$), 6.91–7.26 (multiplet, 8H; 2×Ar$\underline{H}$). F.W.: calc. for C$_{14}$H$_{12}$B$_2$O$_4$=265.87, found m/z 267 (M+1).

Example 15

4,4'-Bi-(phenoxymethyl)-2,2'-1,3,2-dioxaborolane

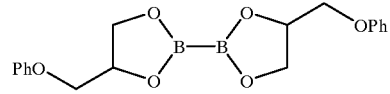

This diboronic ester is prepared following general procedure A using 3-phenoxy-1,2-propanediol. Yield, 71%. $^1$H-nmr (CDCl$_3$, 200 MHz): δ3.96–4.41 (multiplet, 8H; 4×C$\underline{H}_2$O), 4.74–4.86 (multiplet, 2H; 2×OC$\underline{H}$) and 6.86–7.34 (multiplet, 10H; 2×OAr$\underline{H}$). F.W.: calc. for C$_{18}$H$_{20}$B$_2$O$_6$=353.97, found m/z 355 (M+1).

Example 16

4,4,4',4',6,6'-Hexamethyl-2,2'-bi-1,3,2-dioxaborinane

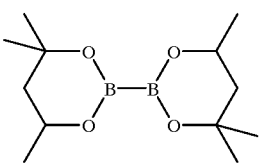

This diboronic ester is prepared following general procedure A using 2-methyl-2,4-pentanediol. Yield, 71%. $^1$H-nmr (CDCl$_3$, 200 MHz): δ1.18–1.32 (multiplet, 18H; 6×C$\underline{H}_3$), 1.44–1.56 (multiplet, 2H; 2×$\underline{H}$CHC), 1.69–1.78 (multiplet, 2H; 2×HC$\underline{H}$C) and 4.07–4.22 (multiplet, 2H; 2×OC$\underline{H}$). F.W.: calc. for C$_{12}$H$_{24}$B$_2$O$_4$=253.94, found m/z 255 (M+1).

Example 17

5,5,5',5'-Tetraethyl-2,2'-bi-1,3,2-dioxaboninane

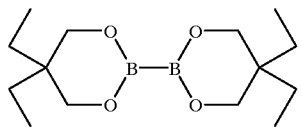

This diboronic ester is prepared following general procedure A using 2,2-diethyl-1,3-propanediol. Yield, 79%. H-nmr (CDCl$_3$, 200 MHz): δ0.75–0.82 (triplet, 12H; 4×C$\underline{H}_3$), 1.25–1.37 (quartet, 8H; 4×C$\underline{H}_2$CH$_3$) and 3.69 (singlet, 8H; 4×C$\underline{H}_2$O). F.W.: calc. for C$_{14}$H$_{28}$B$_2$O$_4$=282.00, found m/z 283 (M+1).

Example 18

4,4',5,5'-Tetramethyl-2,2'-bi-1,3,2-dioxaborolane

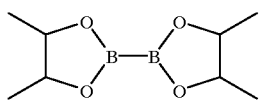

This diboronic ester is prepared following general procedure A using 2,3-butanediol. $^1$H-nmr (CDCl$_3$, 200 MHz): δ1.10–1.28 (multiplet, 12H; 4×C$\underline{H}_3$) and 4.42–4.52 (multiplet, 4H; 4×C$\underline{H}$).

Example 19

4,4'-Dimethyl-2,2'-bi-1,3,2-dioxaborinane

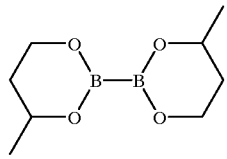

This diboronic ester is prepared following general procedure A using 1,3-butanediol. Yield, 94%. $^1$H-nmr (CDCl$_3$, 200 MHz): δ1.21–1.25 (doublet, 6H; 2×C$\underline{H}_3$), 1.56–1.94 (multiplet, 4H; 2×CH$_2$C$\underline{H}_2$CH) and 3.81–4.14 (multiplet, 6H; 2×OC$\underline{H}_2$ and 2×OC$\underline{H}$). F.W.: calc. for C$_8$H$_{16}$B$_2$O$_4$=197.83, found m/z 199 (M+1).

Example 20

5,5'-Dimethyl-2,2'-bi-1,3,2-dioxaborinane

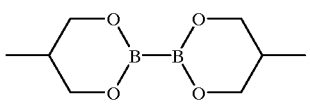

This diboronic ester is prepared following general procedure A using 2-methyl-1,3-propanediol. Yield, 96%. $^1$H-nmr (CDCl$_3$, 200 MHz): δ0.80–0.84 (doublet, 6H; 2×C$\underline{H}_3$), 1.97–2.17 (multiplet, 2H; 2×C$\underline{H}$CH$_3$), 3.43–3.57 (triplet, 4H; 4×$\underline{H}$CHCCH$_3$) and 3.87–3.95 (multiplet, 4H; 4×HC$\underline{H}$CCH3). F.W.: calc. for C$_9$H$_{16}$B$_2$O$_4$=197.83, found m/z 199 (M+1).

Example 21

Bi-(dinaphtho[2,1-d:1,2-f])-2,2'-bi-1,3,2-dioxaborepine

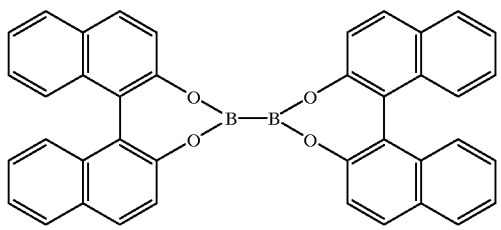

This diboronic ester is prepared following general procedure A using 1,1'-bis-2-naphthol. $^1$H-nmr (CDCl$_3$, 200 MHz): δ6.90–6.95 (multiplet, 2H; Ar$\underline{H}$), 7.12–147.34 (multiplet, 6H; Ar$\underline{H}$) and 7.83–7.99 (multiplet, 2H; Ar$\underline{H}$).

Example 22

6,6'-Diethyl-2,2'-bi-1,3,6,2-dioxazaborocane

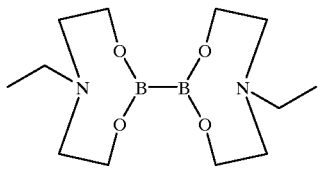

This diboronic ester is prepared following a similar method to that described in general procedure C using N-ethyldiethanolamine, but this time adding the sodium sulphate in the initial stages of the reaction and heating the mixture under reflux. $^1$H-nmr (200 MHz; CDCl$_3$): δ1.15–1.23 (triplet, 6H; 2×C$\underline{H}_3$), 2.88–2.91 (multiplet, 12H; 6×C$\underline{H}_2$N) and 3.83–3.85 (multiplet, 8H; 4×OC$\underline{H}_2$).

Example 23

6,6'-Dimethyl-2,2'-bi-1,3,6,2-dioxazaborocane

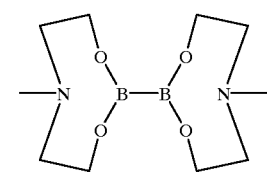

This diboronic ester is prepared following general procedure B using N-methyldiethanolamine. $^1$H-nmr (200 MHz; CDCl$_3$): δ2.51 (triplet, 6H; C$\underline{H}_3$), 2.79–3.35 (multiplet, 8H; 4×C$\underline{H}_2$N) and 3.76–3.94 (multiplet, 8H; 4×C$\underline{H}_2$O).

Example 24

5,5,5',5'-Tetraphenyl-2,2'-bi-1,3,2-dioxaborinane

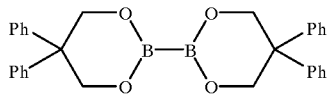

This diboronic ester is prepared following general procedure A using 2,2-diphenyl-1,3-propanediol. $^1$H-nmr (CDCl$_3$, 200 MHz): δ4.48 (singlet, 8H; C$\underline{H}_2$O) and 7.13–7.31 (multiplet, 20H; Ar$\underline{H}$).

Example 25

4,4,4',4',7,7,7',7'-Octamethyl-2,2'-bi-1,3,2dioxaborepane

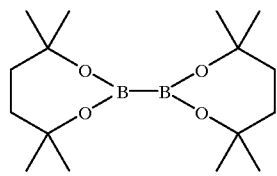

This diboronic ester is prepared following general procedure A using 2,5-dimethyl-2,5-hexanediol. $^1$H-nmr (CDCl$_3$, 200 MHz): δ1.27 (singlet, 24H; C$\underline{H}_3$) and 1,77 (singlet, 8H; C$\underline{H}_2$).

Example 26

1,1,2,2-Tetrakis(neopentyloxy)diborane

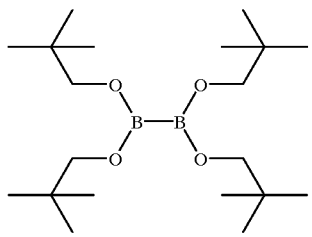

This diboronic ester is prepared following general procedure A using neopentylalcohol. $^1$H-nmr (CDCl$_3$, 200 MHz): δ0.93 (singlet, 36H; C$\underline{H}_3$) and 3.62 (singlet, 8H; C$\underline{H}_2$). F.W.: calc. for C$_{20}$H$_{44}$B$_2$O$_4$=370.19, found (GCMS) m/z=371 (M+1).

Example 27

(4S,4'S,5S,5'S)-Tetramethyl-2,2'-bi-1,3,2-dioxaborolane

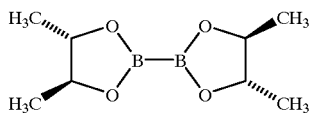

This diboronic ester is prepared following general procedure A using (2S,3S)-(+)-2,3-butanediol. Yield, quantitative. $^1$H-nmr (CDCl$_3$, 200 MHz): δ1.30 (singlet, 6H, C$\underline{H}_3$). 1.33 (singlet, 6H, C$\underline{H}_3$) and 3.99 (multiplet, 4H; C$\underline{H}$). F.W.: calc. for C$_8$H$_{16}$B$_2$O$_4$=197.83, found (GCMS) m/z=199 (M+1).

Example 28

Tetrabutyl (4R,4'R,5R,5'R)-2,2'-bi-1,3,2-dioxaborolane-4,4',5,5'-tetracarboxylate

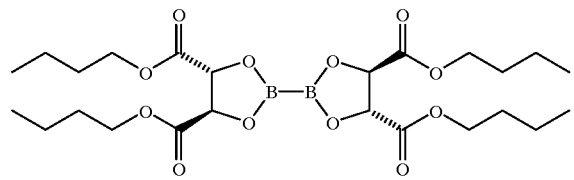

This diboronic ester is prepared following general procedure A using dibutyl L-tartrate. Yield, 93%. $^1$H-nmr (CDCl$_3$, 200 MHz): δ0.89–0.98 (multiplet, 12H; C$\underline{H}_3$), 1.27–1.47 (multiplet, 8H; C$\underline{H}_2$CH$_3$), 1.58–1.72 (multiplet, 8H; CH$_2$C$\underline{H}_2$CH$_2$), 4.15–4.25 (multiplet, 8H; C$\underline{H}_2$O) and 4.92 (singlet, 4H; C$\underline{H}$CO$_2$). The desired compound was detected by GCMS.

Example 29

(4R,4'R,5R,5'R)-N$^4$,N$^4$,N$^{4'}$,N$^{4'}$,N$^5$,N$^5$,N$^{5'}$,N$^{5'}$-Octamethyl-2,2'-bi-1,3,2-dioxaborolane-4,4',5,5'-tetracarboxamide

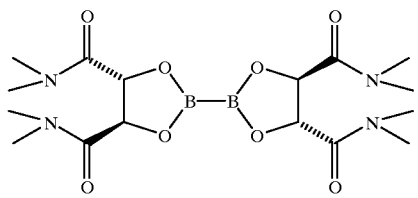

This diboronic ester is prepared following general procedure A using N,N,N',N'-tetramethyl L-tartaramide. Yield, 74%. $^1$H-nmr (CDCl$_3$, 200 MHz): δ2.90 (singlet, 12H; NC$\underline{H}_3$), 3.14 (singlet, 12H; NC$\underline{H}_3$) and 5.54 (singlet, 4H; C$\underline{H}$C=O).

Example 30

4,4,4',4'-Tetramethyl-2,2'-bi-1,3,2-dioxaborinane

Synthesis of

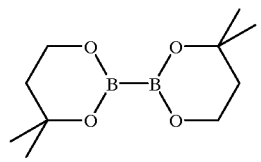

The diol 2-methyl-2,4-dihydroxybutane (1.04 g, 1 mmol) was reacted with diboronic acid (0.45 g, 0.5 mmol) in 25 ml dry THF at room temp. (procedure C without dehydrating agent). The diboronic acid rapidly dissolved to give a colourless, clear solution. The gc on a small aliquot of the reaction solution, diluted with ethyl acetate, showed only two peaks of area ratio 2:98. The weak peak corresponded to the retention time of the diol. On removing the solvent from the reaction solution under reduced pressure the product ester was obtained as a white solid. $^1$H nmr (CDCl$_3$) δ1.30 (s, 12H), 1.78 (t, J=5.8 Hz, 4H), 3.98 (t, J=5.8 Hz, 4H).

Example 31

4,4,4',4',6,6,6',6'-Octamethyl-2,2'-bi-1,3,2-dioxaborinane

Synthesis of

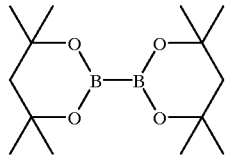

The diol 2,4-dimethyl-2,4-dihydroxypentane (1.32 g, 1 mmol) was reacted with diboronic acid (0.45 g, 0.5 mmol) in 25 ml dry THF at room temp. (procedure C without dehydrating agent). The diboronic acid dissolved to give a colourless, clear solution. The gc on a small aliquot of the reaction solution, diluted with ethyl acetate, showed only two peaks of area ratio 4:95. The weak peak corresponded to the retention time of the diol. On removing the solvent from the reaction solution under reduced pressure the product ester was obtained as a white solid. $^1$H nmr (D$_6$-DMSO) δ1.25 (s, 24H), 1.77 (s, 4H).

Example 32

3,3'-Bi-1,5-dihydro-2,4,3-benzodioxaborepine

Synthesis of

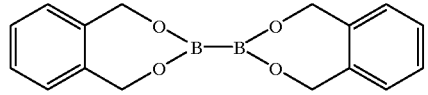

The diol 1,2-benzenedimethanol (1.38 g, 1 mmol) was reacted with diboronic acid (0.45 g, 0.5 mmol) in 25 ml dry THF at room temp. (procedure C without dehydrating agent). After most of the diboronic acid had dissolved, the reaction was warmed to 50–55° C. for several hours and then filtered to give a clear, colourless solution. The solvent was removed from the compound under reduced pressure and a white, soft compound was obtained. $^1$H nmr (CDCl$_3$) gave three broad peaks at δ4.74, 4.89, 5.01 and a sharp singlet at 5.10 (total 8H), and two multiplets at 7.22 and 7.28 (total 8H). The broad peaks sharpened on cooling the CDCl$_3$ solution and are possibly due to isomers of the desired compound.

The formation of the ester, at room temp., is considerably faster in ethanol than in THF, all the diboronic acid (0.45 g, 0.5 mmol) reacting with the diol 1,2-benzenedimethanol (1.38 g, 1 mmol) within several minutes following solvent addition (25 ml) to give a clear, colourless solution. This was stirred at room temperature before removal of the solvent under reduced pressure. A white, hard solid was obtained, free from ethanol ($^1$H nmr) after pumping on the material for several hours at 10$^{-7}$ to 10$^{-1}$ mmHg and temperature around 40° C. $^1$H nmr (CDCl$_3$) δ4.73(s), 5.09(s) (intensity ratio 1:4.3, total 8H,), and 7.23 and 7.32 (total 8H). The peaks at δ4.73 and 7.31 are weak and may be due to an isomer of the product in which the ligands bridge the two boron atoms.

Example 33

4,4,4',4',5,5'-Hexamethyl-2,2'-bi-1,3,2-dioxaborolane

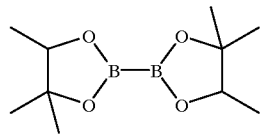

This diboronic ester is prepared following general procedure A using 2-methyl-2,3-butanediol. $^1$H-nmr (CDCl$_3$, 200 MHz): δ0.75–1.18 (multiplet, CH$_3$ and CH). F.W.: calc. for C$_{10}$H$_{20}$B$_2$O$_4$=225.89, found (GCMS) m/z=226 (M+1).

Example 34

4,4',4'-Tetramethyl-2,2'-bi-1,3,2-dioxaborolane

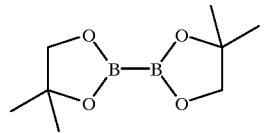

This diboronic ester is prepared following general procedure A using 2-methylpropane-1,2diol. $^1$H-nmr (CDCl$_3$, 200 MHz): δ1.22 (singlet, 12H; CH$_3$) and 3.73 (singlet, 4H; CH$_2$). F.W.: calc. for C$_8$H$_{16}$B$_2$O$_4$=197.83, found (GCMS) m/z=198 (M+1).

TABLE 1

| Compound | IUPAC Nomenclature: Compound Name |
|---|---|
| Example 1 | (4R,4'R,5R,5'R)-Tetramethyl-2,2'-bi-1,3,2-dioxaborolane. |
| Example 2 | 1,1,2,2-Tetrakis(2-methoxyethyloxy)diborane. |
| Example 3 | Bis((1S,2S,3R,5S)-(+)-pinanediolato)diboron(B—B). |
| Example 4 | (4R,4'R)-Diphenyl-2,2'-bi-1,3,2-dioxaborolane. |
| Example 5 | 4,4'-Bi-[(4-methoxyphenoxy)methyl]-2,2'-bi-1,3,2-dioxaborolane. |
| Example 6 | 2,2'-Bi-(3aR,7aS)hexahydro-1,3,2-benzodioxaborole. |
| Example 7 | Tetraisopropyl (4R,4'R,5R,5'R)-2,2'-bi-1,3,2-dioxaborolane-4,4'5,5'-tetracarboxylate. |
| Example 8 | (3aR,3'aR,6aS,6'aS)-Di-(tetrahydro-3aH-cyclopenta[d])-2,2'-bi-1,3,2-dioxaborolane. |
| Example 9 | (3R,6S,3'R,6'S)-Di-(tetrahydrofuro[3,4-d])-2,2'-bi-1,3,2-dioxaborolane. |
| Example 10 | 4,4'-Bis(methoxymethyl)-2,2'-bi-1,3,2-dioxaborolane. |
| Example 11 | 2,2'-Bi-1,3,2-dioxaborepane. |
| Example 12 | 5,5'-Dihydroxymethyl-5,5'-Dimethyl-2,2'-bi-1,3,2-dioxaborinane. |
| Example 13 | Bis(1R,2R,3S,5R-(-)-pinanediolato)diboron(B—B). |
| Example 14 | 2,2'-Bi-4H-1,3,2-benzodioxaborinine. |
| Example 15 | 4,4'-Bi-(phenoxymethyl)-2,2'-1,3,2-dioxaborolane. |
| Example 16 | 4,4,4',4',6,6'-Hexamethyl-2,2'-bi-1,3,2-dioxaborinane. |
| Example 17 | 5,5,5',5'-Tetraethyl-2,2'-bi-1,3,2-dioxaborinane. |
| Example 18 | 4,4',5,5'-Tetramethyl-2,2'-bi-1,3,2-dioxaborolane. |
| Example 19 | 4,4'-Dimethyl-2,2'-bi-1,3,2-dioxaborinane. |
| Example 20 | 5,5'-Dimethyl-2,2'-bi-1,3,2-dioxaborinane. |
| Example 21 | Bi-(dinaphtho[2,1-d: 1,2-f])-2,2'-bi-1,3,2-dioxaborepine. |
| Example 22 | 6,6'-Diethyl-2,2'-bi-1,3,6,2-dioxazaborocane. |
| Example 23 | 6,6'-Dimethyl-2,2'-bi-1,3,6,2-dioxazaborocane. |
| Example 24 | 5,5,5',5'-Tetraphenyl-2,2'-bi-1,3,2-dioxaborinane. |
| Example 25 | 4,4,4',4',7,7,7',7'-Octamethyl-2,2'-bi-1,3,2dioxaborepane. |
| Example 26 | 1,1,2,2-Tetrakis(neopentyloxy)diborane. |
| Example 27 | (4S,4'S,5S,5'S)-Tetramethyl-2,2'-bi-1,3,2-dioxaborolane. |

TABLE 1-continued

IUPAC Nomenclature:

| Compound | Compound Name |
|---|---|
| Example 28 | Tetrabutyl (4R,4'R,5R,5'R)-2,2'-bi-1,3,2-dioxaborolane-4,4',5,5'-tetracarboxylate. |
| Example 29 | (4R,4'R,5R,5'R)-$N^4,N^4,N^{4'},N^{4'}$,$N^5,N^5,N^{5'},N^{5'}$-Octamethyl-2,2'-bi-1,3,2-dioxaborolane-4,4',5,5'-tetracarboxamide. |
| Example 30 | 4,4,4',4'-Tetramethyl-2,2'-bi-1,3,2-dioxaborinane. |
| Example 31 | 4,4,4',4',6,6,6',6'-Octamethyl-2,2'-bi-1,3,2-dioxaborinane. |
| Example 32 | 3,3'-Bi-1,5-dihydro-2,4,3-benzodioxaborepine. |
| Example 33 | 4,4,4',4',5,5'-Hexamethyl-2,2'-bi-1,3,2-dioxaborolane. |
| Example 34 | 4,4,4',4'-Tetramethyl-2,2'-bi-1,3,2-dioxaborolane. |

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in the specification, individually or collectively, and any and all combinations of any two or more of said steps or features.

What is claimed is:

1. A process for the preparation of a diboronic acid ester comprising contacting tetrahydroxydiboron with a suitable monoalcohol, diol or polyol in the presence of an appropriate solvent or mixture of solvents and at a temperature between room temperature and the boiling point of the solvent at ambient pressure such that the tetrahydroxydiboron reacts with the monoalcohol, diol or polyol to form the diboronic acid ester.

2. A process according to claim 1 wherein the tetrahydroxydiboron is reacted with a diol or polyol in a solvent comprising a monoalcohol.

3. A process according to claim 2 wherein the monoalcohol is a lower alkanol.

4. A process according to claim 3 wherein at least four equivalents of monoalcohol are used and the product formed between the tetrahydroxydiboron and the monoalcohol reacts with the diol or polyol by transesterification to thereby form the diboronic acid ester.

5. A process according to claim 3 wherein the lower alkanol is methanol or ethanol.

6. A process according to claim 1 performed in the absence of an acid catalyst.

* * * * *